United States Patent [19]

Ranki et al.

[11] Patent Number: 4,486,539

[45] Date of Patent: Dec. 4, 1984

[54] DETECTION OF MICROBIAL NUCLEIC ACIDS BY A ONE-STEP SANDWICH HYBRIDIZATION TEST

[75] Inventors: Tuula M. Ranki; Soderlund Hans E., both of Espoo, Finland

[73] Assignee: Orioon Corporation Ltd., Finland

[21] Appl. No.: 434,182

[22] Filed: Oct. 14, 1982

[30] Foreign Application Priority Data

Oct. 16, 1981 [FI] Finland ................... 813251

[51] Int. Cl.$^3$ ............................................. C12N 15/00
[52] U.S. Cl. ................................... 436/504; 436/804; 436/808; 935/78
[58] Field of Search ............... 536/29, 27; 435/6, 253, 435/317, 270, 810; 422/61; 424/1.1; 436/501, 503, 504, 94, 804, 808-810

[56] References Cited

U.S. PATENT DOCUMENTS

| 4,139,346 | 2/1979  | Rabbani       | 422/56   |
| 4,302,204 | 11/1981 | Wahl et al.   | 23/230.3 |
| 4,358,535 | 11/1982 | Falkow et al. | 435/5    |
| 4,359,535 | 11/1982 | Pieczenik     | 435/317  |

OTHER PUBLICATIONS

Dunn, A. R., et al., *Methods in Enzymology*, vol. 65 (7), pp. 448-478 (1980).
Dunn, A. R., et al., "Cell," vol. 12, pp. 23-36 (9-1977).
Dunn, A. R., et al, "Cell," vol. 15, pp. 23-36 (1978).
Kimmel, A. R., et al., "Cell," vol. 16 (4) pp. 787-796 (1979), Abstract.
Long, E. O., et al., "Cell," vol. 18 (4) pp. 1185-1196), (1979).
Gillis, M., et al., International J. of Systematic Bacteriology, vol. 30 (1) pp. 7-27 (1-1980).
Brautgam, A. R., et al., J. Clinical Microbiology, vol. 12, (2) pp. 226-234 (8-1980).
Gillespie, D., et al., J. Mol. Biology, 12(3), 829-842, (1965).
Warnaar, A. O. et al., Biochem. Biophys. Res. Comm. vol. 24 (4), pp. 554-558.
Grunstein, M., et al., Proc. Nat'l. Acad. Sci. vol. 72 (10), pp. 3961-3965 (10-1975).
Brandsma et al., Proc. Natl. Acad. Sci. USA, vol. 77 (11), pp. 6851-6855 (11-1980).
Owens et al., Science/213 (4508), pp. 670-672 (8-7-1981).

*Primary Examiner*—Christine M. Nucker
*Assistant Examiner*—M. Moskowitz
*Attorney, Agent, or Firm*—Brumbaugh, Graves, Donohue & Raymond

[57] ABSTRACT

This invention relates to a diagnostic kit based on a one step hybridization procedure and method of using the kit for identifying the nucleic acids of viruses and bacteria contained in a single sample. The procedure requires two nucleic acid reagents for each microbe or group of microbes to be identified.

8 Claims, No Drawings

4,486,539

DETECTION OF MICROBIAL NUCLEIC ACIDS BY A ONE-STEP SANDWICH HYBRIDIZATION TEST

BACKGROUND OF THE INVENTION

The present invention relates to a kit for the detection of microbes using a two step hybridization procedure.

In traditional microbial diagnostics the presence of a microbe in a given sample is demonstrated by isolating the microbe in question. After enrichment cultivations, the microbe is identified either on the basis of its biochemical properties or its immunological properties. Both methods of identification require that the microbe in the sample be viable. Such identification can be laborious and time-consuming. Indeed, the detection of certain viruses, requiring sophisticated biochemical purification or tissue culture techniques, can take as long as 4 to 6 weeks.

The purpose of this invention is to provide a diagnostic kit for detecting the nucleic acid of a microbe in a sample with the aid of a sensitive and specific nucleic acid hybridization technique. The nucleic acid may be of two types, deoxyribonucleic acid (DNA) or ribonucleic acid (RNA).

Nucleic acid hybridization is an old and well known method for investigating the identity of nucleic acids. Hybridization is based on complementary base pairing. When single-stranded nucleic acids are incubated in solution, complementary base sequences pair to form double-stranded stable hybrid molecules. The double-stranded hybrid molecules can be separated from the single-stranded molecules by chemical means.

Some methods based on the identification of nucleic acid(s) have already been applied to microbial diagnostics. Enterotoxigenic *Escherichia coli* has been identified from fecal samples by colony hybridization using the gene for toxin production as a probe. Positive hybridization has been demonstrated by autoradiography (see Moseley et al., *Journal of Infectious Diseases*, Vol. 142, pp. 892–898 (1980). Grunstein and Hogness have reported a method for detecting nucleic acids by colony hybridization in *Proc. Natl. Acad. Sci. USA*, Vol. 72, pp. 3961–3965 (1975). Hybridization has also been used as a method to distinguish between Herpes simplex virus type 1 and 2 after enrichment cultivation (see Brautigam et al., *Journal of Clinical Microbiology*, Vol. 12, pp. 226–234 (1980). In the latter method, the double-stranded hybrid was separated from the single-stranded nucleic acid by affinity chromatography.

Brandsma and Miller have identified DNA from cells infected with Epstein-Barr virus by hybridizing filters containing immobilized Epstein-Barr virus DNA with a radioactive probe, positive hybridization being detected by autoradiography as described in *Proc. Natl. Acad. Sci. USA*, Vol. 77, pp. 6851–6855 (1980).

The present invention utilizes the two step hybridization technique, also called the sandwich hybridization technique, described by Dunn and Hassell in *Cell*, Vol. 12, pp. 23–36 (1977).

SUMMARY OF THE INVENTION AND DESCRIPTION OF THE PREFERRED EMBODIMENTS

A highly sensitive method has been developed for the detection of nucleic acids. A given microbe or microbial group can be detected from a sample of nucleic acid rendered single-stranded. The method requires two nucleic acid reagents for each microbe or group of microbes to be identified. The reagents are two separate nucleic acid fragments derived from the genome of the microbe to be identified, which fragments have no sequences in common but preferably are situated close together in the genome and produced by using the established recombinant DNA techniques. One of the nucleic acid fragments is fixed to a solid carrier, preferably a nitrocellulose filter, after being denaturated and the other fragment, also in single-stranded form, is labelled with a suitable label. When the nucleic acids to be identified are contacted with the nucleic acid fragments on the solid carrier, complementary base pairs anneal forming a hybrid. The hybrids formed on the solid carrier are labelled by annealing the second nucleic fragment which has been labelled to the single-stranded nucleic acid sample to be identified. The labelled nucleic acid fragments only hybridize to the correct single-stranded nucleic acids originating from the sample. Thus only those carriers to which the complementary nucleic acids from the sample have hybridized can become labelled. These carriers are easily washed and the label is measured by established methods.

The kit described in this invention can in principle be used for the identification of DNA- or RNA-containing organisms, such as viruses, bacteria, fungi and yeasts. The kit has the specific advantage of simultaneously detecting specific bacteria and viruses from a mixed sample regardless of whether the microbes contain DNA or RNA. By suitable combination of reagents it is possible to develop kits such that each microbe to be identified has its own specific solid carrier and labelled nucleic acid reagent. All the filters included in the reagent combination can be added to the sample simultaneously, along with the labelled nucleic acid reagents. When hybridization has taken place, the solid carriers are washed and their labelling is measured. The technique is highly specific since the carriers are labelled by complementary base pairing.

Kits of this invention can be used, e.g. in medical microbiology, veterinary microbiology and food hygiene investigations and microbial diagnostics of plant diseases. Suitable sample materials are animal and plant tissue homogenates, blood, feces and nasal and urethral mucous. It can be estimated that the kit is sufficiently sensitive to detect microbe levels normally present in clinical samples. Preliminary enrichment of the microbe present in the sample by cultivation is of course possible before the identification test and in some cases would be essential. The kit is also suitable for the investigation of samples from which the microbe can no longer be cultivated but which contain considerable amounts of microbial debris (e.g. after the commencement of antibiotic treatment), or when cultivation of the microbe is particularly laborious and difficult (e.g. anaerobic bacteria, which are present in large numbers in suppurative samples in the case of infections caused by anaerobes).

Diagnostic kits of the invention can be used to detect the nucleic acid(s) present e.g. in the following:

Respiratory infections:
 (a) Bacteria: β-hemolytic streptococci (group A), *Hemophilus influenzae*, pneumococci, *Mycoplasma pneumoniae*, mycobacteria
 (b) Viruses: influenza A, influenza B, parainfluenza (types 1, 2 and 3), respiratory syncytial virus, adenoviruses, coronaviruses, rhinoviruses Diarrhoeas:

(a) Bacteria: salmonellae, shigellae, *Yersinia enterocolitica*, enterotoxigenic, *E. coli, Clostridium difficile,* campylobacter (b) Viruses: rotaviruses, parvoviruses, adenoviruses, enteroviruses Venereal diseases:

(a) Bacteria: *Neisseria gonorrhoeae, Treponema pallidum, Chlamydia trachomatis*

(b) Viruses: Herpes simplex virus (c) Yeasts: *Candida albicans*

(d) Protozoa: *Trichomonas vaginalis*

Sepsis:

(a) Bacteria: β-hemolytic streptococci (group A), pneumocci, enterobacteria

Food hygiene:

(a) Bacteria: salmonellae and *Clostridium perfringens.*

The specificity of the diagnostic kit can be limited to a defined microbial group (e.g. salmonella bacteria) or broadened to a wider microbial group (e.g. enterobacteriaceae) by selecting particular nucleic acid fragments.

The nucleic acid reagents required in the sandwich hybridization technique are produced by recombinant DNA technology. The following describes the reagent production and test procedures for Example 1.

REAGENTS

Adenovirus type 2 (Ad$_2$) (ATCC VR-846) was from KTL, the Public Health Laboratory located in Helsinki, Finland. Ad$_2$ was cultivated and purified and its DNA was isolated in accordance with the procedure set forth by Petterson and Sambrook in the *Journal of Molecular Biology,* Vol. 73, pp. 125–130 (1973). The DNA was digested with BamHI-restriction enzyme obtained from Bethesda Research Laboratories (BRL), which enzyme cuts the DNA into four reproducible fragments. Two of these fragments were inserted into the BamHI-site of the vector plasmid pBR322 (BRL) with the aid of T-4-ligase (BRL). The fragments were not separated before ligation, but the insert was in each case identified only after cloning. The bacterial host, *E. coli* HB101 (K12) gal$^-$, pro$^-$, leu$^-$, hrs$^-$, hrm$^-$, recA, str$^R$, F$^-$, obtained from KTL, was transformed with the plasmid DNA composed of recombinant plasmids, i.e. molecules which had accepted fragments of the adenovirus DNA, by the procedure set forth in Cohen et al. in *Proc. Natl. Acad. Sci. USA,* Vol. 69, pp. 2110–2114 (1972).

Bacterial clones which contained recombinant plasmids were chosen. Ampicillin and tetracycline resistance were transferred to the bacterium by the pBR322-plasmid (Bolivar et al., *Gene,* Vol. 2, pp. 95–113 (1977)). Bacteria containing the recombinant plasmid were sensitive to tetracycline, because the BamHI-restriction site was within the tetracycline gene and the foreign DNA inserted into this region destroyed the gene. The insert of the plasmid was characterized after plasmid enrichment by determining the size of the restriction fragments after BamHI digestion using agarose gel electrophoresis. Adjacent BamHI D- and C-fragments of the Ad$_2$DNA were chosen as reagents (Soderlund et al., *Cell,* Vol. 7, pp. 585–593 (1976)).

The preferred recombinant plasmids, Ad$_2$C-pBR322, KTL deposit No. E231, and Ad$_2$D-pBR322, KTL deposit No. EH230, were cultivated and purified as described in the literature by Clewell and Helinski in *Proc. Natl. Acad. Sci. USA,* Vol. 62, pp. 1159–1166 (1969).

The recombinant plasmid Ad$_2$D-pBR322 was used as the filter reagent. It was not necessary for purposes of the invention to remove the plasmid sequences since the sample(s) did not contain pBR322 sequences. However, for the radioactive labelling, the nucleic acid was separated from pBR322-DNA after BamHI-digestion with the aid of agarose gel electrophoresis. The C-fragment was isolated from LGT-agarose (Marine Colloids, Inc.) by phenol extraction or electro-elution (Wieslander, *Anal. Biochem.,* Vol. 98, pp. 305–309 (1979) and concentrated by ethanol precipitation.

It was particularly expedient to subclone the nucleic acid fragment chosen for labelling in a separate vector, in order to avoid the hybridization background resulting from the direct hybridization with the filter of the residual plasmid sequences, contaminating the labelled nucleic acid reagent. The single-stranded DNA-phage M13 mp7 (BRL) could be used as an optimal vector (Messing et al., *Nucleic Acids Research,* Vol. 9, pp. 309–323 (1981)).

ATTACHMENT OF DNA TO THE FILTER

The recombinant plasmid Ad$_2$D-pBR322 was denatured to a single stranded form and nicked randomly at several sites by treatment with 0.2N NaOH for 5 minutes at 100° C., whereafter the DNA was chilled and, immediately prior to transference to the filter, neutralized and pipetted to the transfer solution, 4×SSC medium on ice (SSC=0.15M NaCl, 0.015M Na-citrate). The filters (Schleicher and Schull BA85 nitrocellulose) were thoroughly wetted in 4×SCC solution for about 2 hours before the application of DNA. The DNA was attached to the filter in a dilute solution (0.5–1.0 μg/ml) by sucking the solution through the filter in a weak vacuum. The filter was capable of absorbing DNA up to about 180 μg/cm$^2$ (see Kafatos et al., *Nucleic Acids Research,* Vol. 7, pp. 1541–1552 (1979)). DNA-concentrations of between 0.5 μg DNA/2.5 cm diameter of filter and 1.0 μg DNA/0.7 cm diameter of filter were used. After DNA-filtration the filters were washed in 4×SSC, dried at room temperature and finally baked in a vacuum oven at 80° C. for 2 hours. Since the DNA on the filters was stable, the filters were stored for long periods at room temperature (Southern, *Journal of Molecular Biology,* Vol. 98, pp. 503–517 (1975)).

LABELLING OF THE RADIOACTIVE NUCLEIC ACID FRAGMENT

The radioactive label used was the $^{125}$I-isotope, which was quantitated by gamma counters. Since the half-life of the isotope is 60 days, the utilization period of $^{125}$I-labelled reagents is about 4 months.

"NICK-TRANSLATION" LABELLING

This method displaces one of the nucleotides in the nucleic acid with a radioactive one, whereby upon replication the whole DNA molecule is labelled. This was carried out according to the method published by Rigby et al. in the *Journal of Molecular Biology,* Vol. 113, pp. 237–251 (1977). The DNA was labelled in a solution containing a $^{125}$I-labelled deoxynucleoside triphosphate such as $^{125}$I-dCTP (Radiochemical Centre, Amersham: >1500 Ci/mmol) as substrate. Under optimal conditions a specific activity of 10$^9$ cpm/μg DNA was obtained. The labelled DNA was purified from nucleotides remaining in the reaction mixture by simple gel filtration, e.g. using BioGel P30 (BioRad).

OTHER LABELLING METHODS

The single-stranded nucleic acid reagent produced in M13 mp7-phage was labelled by chemical iodination, in which the reactive $^{125}$I was added covalently to the nucleic acid (see Commerford, *Biochemistry*, Vol. 10, pp. 1993-2000 (1971) and Orosz et al., *Biochemistry*, Vol. 13, pp. 5467-5473 (1974)). Alternatively, the nucleic acid was made radioactive by end-labelling with radioactive nucleotides by the terminal transferase (see Roychoudhury et al., *Methods of Enzymology*, Vol. 65, pp. 43-62 (1980)).

The reagent preparation described above has related to microbes whose genetic material is in the form of DNA. In the case of RNA viruses, the cloning of genome fragments took place after a DNA copy (cDNA) of the virus RNA was made with the aid of reverse transcriptase, followed by DNA-polymerase, to copy the second DNA strand, thereafter the DNA was cloned as described above (see Salser, *Genetic Engineering*, Ed. Chakrabarty, CRC Press, pp. 53-81 (1979)).

The most suitable cloning method is chosen depending on the microbe used. The hosts as well as the vectors vary. For example, vector possibilities include the λ-phage, other plasmids, cosmids, cloning e.g. in *Bacillus subtilis* bacteria, etc. (Recombinant DNA, *Benchmark Papers in Microbiology*, Vol. 15, Eds. Denniston and Enqvist, Dowden, Hutchinson and Ross, Inc. (1981) and Ish-Horowicz et al., *Nucleic Acids Research*, Vol. 9, pp. 2989-2998 (1981)).

PERFORMANCE OF THE TEST

Sample treatment

The microbial nucleic acid to be identified was released from the microbe itself and also from the infected cells, after which it was denatured to a single-stranded form. Virus genomes were isolated by treating the viral sample material with 1% sodium dodecylsulphate (SDS) and the proteins which protect the viral genome were removed by proteinase K treatment (1 mg/ml, 37° C., 60 minutes). Bacteria were disrupted by lysozyme and EDTA treatment.

If the sample contains large quantities of viscous high molecular weight cellular DNA, the cellular DNA is sheared at a few sites in order to reduce its viscosity, e.g. by sonication or by passing the sample a few times through a fine needle. Hybridization The hybridization occurred in 50% formamide (deionized, stored at −20° C.) 4×SSC Denhardt solution, containing 1% SDS and 0.5 mg/ml DNA (salmon sperm or calf thymus), at 37° C. and for 16-20 hours. (See Denhardt, *Biochem. Biophys. Research Communications*, Vol. 23, pp. 641-646 (1966)). The filters chosen for the hybridization were incubated in a suitable vessel to which the hybridization mixture was added. The hybridization mixture contained a pretreated sample of bacteria or virus to which was added the radioactive nucleic acid reagent(s). The mixture was denaturated by boiling for 5 minutes followed by quick cooling at 0° C. Concentrated formamide, SSC and Denhardt solutions, were added with mixing to the denatured and cooled nucleic acid mixture. The hybridization mixture was pipetted onto the filters in the hybridization vessel. After hybridization the filters were carefully washed and counted individually in the gamma counter.

The invention is illustrated by the following examples:

EXAMPLE 1

The sandwich hybridization method in accordance with the invention detected viral DNA in a solution as well as viral DNA in infected cells.

HeLa cells were infected with type 2 adenovirus. The cells were then disrupted by treatment with 1% SDS, followed by digestion with 1 mg/ml proteinase K enzyme (Sigma) for 30 minutes at 37° C. Before denaturation the sample was passed through a fine needle. For the details concerning the filters, nucleic acid reagents and hybridization, refer to the text of Table 1.

TABLE 1

| Samples | Filters (cpm) | | |
|---|---|---|---|
| | Adeno (1) | Calf thymus (2) | Blank (3) |
| Adenovirus type 2 DNA (BRL) (500 ng) | 9000 | 49 | — |
| HeLa cells (6 × 10$^5$) infected with adenovirus | 8200 | — | — |

Filters:
(1)Ad$_2$D-pBR322-plasmid, 2 μg
(2)Calf thymus DNA 1 μg (Boehringer Mannheim)
(3)Blank (no DNA)

Labelled nucleic acid reagent:
Ad$_2$-BamHI C-fragment, purified, specific activity 90×10$^6$ cpm/μg (200000 cpm $^{125}$I/reaction)

Hybridization:
50% formamide, 4×SSC, Denhardt solution, containing 0.5 mg/ml salmon sperm DNA and 1% SDA for 16 hours at 30° C.

Washing:
0.1×SSC for 40 minutes at room temperature

Adenovirus DNA fragments hybridized to adenovirus type 2 DNA and to adenovirus DNA from HeLa cells infected with adenovirus as shown in the above Table 1. The hybridization background radiation was measured in a tube containing only the filter and the labelled nucleic acid reagent, without the sample. The background radiation came from the pBR322 sequence which occurred in the labelled nucleic acid reagent. These sequences hybridized directly with the filter without the mediation of the sample. The filters containing calf thymus and no DNA were used in the test as controls, indicating on the one hand the specificity of hybridization and on the other the level of the nonspecific background radiation arising, e.g. from insufficient washing. The values appearing in Table 1 were corrected by subtraction of the reagent background, obtained by carrying out a similar hybridization but without sample. The background due to the reagents was subtracted from the cpm-values hybridized to the filters.

EXAMPLE 2

The sandwich hybridization method in accordance with the invention detected viral RNA in solution and in infected cells.

The model single-stranded RNA-virus used was the Semliki Forest virus, prototype strain, obtained from the London School of Hygiene and Tropical Medicine. Using the virus genome as a template cDNA was produced, which was cloned into the pstI site of pBR322 plasmid as described by Garoff et al. in *Proc. Natl. Acad. Sci. USA*, Vol. 77, pp. 6376-6380 (1980). The recombinant plasmid, called pKTH312, was deposited at KTL under deposit No. EH 232. The insert of this plasmid, originating from the virus genome, is about 1400 nucleotides long, and is derived from the structural protein area, approximately from nucleotide 200 to nucleotide 1600. The whole recombinant plasmid pKTH312 was linearized with EcoRI restriction enzyme (BRL) since the sequence originating from the Semliki Forest virus did not contain recognition sites for the EcoRI-enzyme. The linearized plasmid was cut into two fragments using XhoI-enzyme (BRL). The restriction site of the latter was located within the Semliki Forest virus sequence. The larger EcoRI-XhoI-fragment A (about 3900 base pairs) was attached to the filter and the smaller fragment B (about 1850 base pairs) was labelled with $^{125}$I using the nick-translation technique.

BHK-21 cells were infected with Semliki Forest virus. Semliki Forest virus (30 μg) was disrupted with SDS before the test. The infected cells were handled as described in Table 1.

TABLE 2

| Samples | Filters (cpm) | | |
|---|---|---|---|
| | Semliki Forest virus (1) | Calf thymus (2) | Blank (3) |
| Semliki Forest virus 30 μg | 3340 | — | 33 |
| Cells infected with Semliki Forest virus (5 × 10$^5$) | 2698 | 8 | 10 |
| Non-infected cells | 10 | 5 | 8 |

Filters:
(1)EcoRI-XhoI-fragment A (1.2 μg) of the pKTH312 plasmid
(2)Calf thymus DNA 1 μg
(3)Blank (no DNA)

Labelled nucleic acid reagents:
EcoRI-XhoI-fragment B of the plasmid pKTH312, specific activity 90×10$^6$ cpm/μg DNA (200,000 cpm $^{125}$I/reaction).
Hybridization:
See text of Table 1.
Washing:
See text of Table 1.

Semliki Forest virus specific fragments hybridized to Semliki Forest virus RNA and to Semliki Forest virus RNA from the BHK-21 cells infected with Semliki Forest virus as shown in the above Table 2. The values given in the table have been corrected for reagent background, obtained from a similar hybridization without sample.

EXAMPLE 3

Viral messenger RNA was detected in solution and in infected cells with the aid of the sandwich hybridization method.

The filter hybridization reagents were produced from SV40-virus DNA (BRL) by cutting the DNA into two parts using PstI-enzyme (Boehringer Mannheim) as described by Lebowitz and Weissman in *Current Topics in Microbiol. Immunol.*, Vol. 87, pp. 43–712 and the fragments were isolated and purified by agarose gel electrophoresis. Fragment A (4000 base pairs) was radioactively labelled with $^{125}$I by nick-translation and fragment B (1220 base pairs) was attached to the filter.

The DNA fragments were chosen so that each contained areas coding for both early and late messengers. Thus fragment B contained about 700 bases from the structural protein gene VP1 and over 600 bases from the gene for early messengers. Because the DNA of SV40 virus is in itself a covalently closed ring, it cannot be detected by the test before linearization. Therefore, when infected cells were used as the sample it was possible to test how well the method was adaptable to the detection of RNA copies of the viral genome. As can be seen from the results in Table 3, the test was excellently suited to the investigation of infected cells. The table also demonstrated that the same reagents could be used to investigate both the viral DNA and mRNA made from it.

SV40-virus DNA (BRL) was linearized with EcoRI restriction enzyme (BRL). CV1-cells (Biomedical Centre, Upsala University) were infected with SV40-virus (obtained from Chou and Martini, NIH, Bethesda) and the cells were harvested 40 hours after infection. Treatment of the sample was as described in Table 1.

TABLE 3

| Samples | Filters (cpm) | | |
|---|---|---|---|
| | SV40 (1) | Calf thymus (2) | Blank (3) |
| Test 1 | | | |
| SV40 viral DNA (50 ng) (linearized) | 20061 | 159 | 104 |
| No sample | — | — | — |
| Test 2 | | | |
| CV1-cells infected with SV40-virus 40 hours after infection (10$^6$ cells) | 30814 | 294 | 580 |
| Non-infected cells | — | — | — |

Filters:
(1)The shorter fragment PstI B (0.2 μg) of the circular SV40-virus DNA digested with PstI-restriction enzyme
(2)Calf thymus DNA 1 μg
(3)Blank (no DNA)

Labelled nucleic acid reagent:
The longer PstI A-fragment of the SV40-virus DNA, specific activity 28×10$^6$ cpm/μg DNA (200,000 cpm $^{125}$I/reaction)
Hybridization:
See text of Table 1. The time for the hybridization was 40 hours.
Washing:
See text of Table 1.

SV40 fragments hybridized to SV40 viral DNA and to viral DNA from CV-1 cells infected with SV40 virus as shown in Table 3. The values presented in the table have been corrected for reagent background, obtained from a similar hybridization carried out without sample.

EXAMPLE 4

*Bacillus amyloliquefaciens* was detected by sandwich hybridization.

The reagents were fragments of the α-amylase gene of *B. amyloliquefaciens* E18 (Technical Research Centre of Finland, VTT), which were isolated for the purpose of this test from the recombinant plasmid pKTH10 (see Palva et al., *Gene*, Vol. 15, pp. 43–51 (1981)) by treatment with restriction enzyme and subsequent agarose gel electrophoresis. The fragments used for this test were the ClaI-EcoRI fragment (460 base pairs) (ClaI Boehringer Mannheim) and the EcoRI-BamHI fragment (1500 base pairs). The EcoRI-BamHI fragment was attached to the filter and the ClaI-EcoRI fragment was labelled with $^{125}$I by nick-translation.

Bacterial samples were treated with lysozyme (67 μg/ml) for 30 minutes at 37° C. and 5 mM EDTA was added to the *E. coli* samples. SDS was added to all the samples (final concentration 12%) and the samples were passed twice through a fine needle to reduce their viscosity before being denatured by boiling as described in the text relating to handling of samples.

As can be seen from Table 4, the *B. amyloliquefaciens* was identifiable by sandwich hybridization on the basis of the single α-amylase gene. *E. coli* gave a result in this test which was indistinguishable from the background.

TABLE 4

| Samples | Filters (cpm) | | |
|---|---|---|---|
| | α-amylase (1) | Calf thymus (2) | Blank (3) |
| pKTH10-plasmid-DNA (linearized) 1 μg | 5773 | 47 | — |
| No sample | — | — | — |
| *E. coli* HB101 (10$^9$) | — | — | — |
| *Bacillus amylolique-faciens* (3 × 10$^9$) | 3377 | — | — |
| *Bacillus amylolique-faciens* (10$^9$) | 2871 | — | — |

Filters:
(1)The EcoRI-BamHI fragment of the α-amylase gene from plasmid pKTH10, 0.35 μg
(2)Calf thymus DNA, 1 μg
(3)Blank (no DNA)

Labelled nucleic acid reagent:
The ClaI-EcoRI fragment of the α-amylase gene from plasmid pKTH10, specific activity 35 × 10$^6$ cpm/μg (200,000 cpm $^{125}$I/reaction)
Hybridization:
See text of Table 1.
Washing:
See text of Table 1.
The values appearing in the table have been corrected for reagent background, obtained from a similar hybridization without sample.

EXAMPLE 5

A reagent combination kit in accordance with the invention detected specific viral and bacterial nucleic acids in a given sample.

The samples investigated in this test were cells infected by three viruses (adenovirus, SV40 virus and Herpex simplex virus) and a sample containing *Bacillus amyloliquefaciens* bacteria. As shown in Table 5, the following reagents were all simultaneously added to each sample: 5 filters, each containing one type of DNA from SV40 virus, adenovirus, *Bacillus amyloliquefaciens*, α-amylase gene and calf thymus, a filter containing no DNA at all, and 200,000 cpm of each of the following labelled nucleic acid reagents: SV40 virus, adenovirus and α-amylase gene DNA reagent.

Cell samples infected with SV40 virus and adenovirus have been described in Tables 3 and 1, respectively. 10$^6$ Vero cells were infected with Herpes simplex virus type 1. The cells were harvested 20 hours post infection when cytopathic effect was observed.

TABLE 5

| Samples | Filters (cpm) | | | | |
|---|---|---|---|---|---|
| | SV40 (1) | Adeno (2) | α-amylase (3) | Calf thymus (4) | Blank (5) |
| Cells infected with SV40 virus (10$^6$) | 18390 | 2 | 13 | 22 | 31 |
| Cells infected with adenovirus type 2 (6 × 10$^5$) | — | 8750 | 5 | 13 | — |
| Cells infected with Herpex simplex virus (10$^6$) | — | — | — | 5 | 13 |
| *Bacillus amylolique-faciens* (10$^9$) | 15 | 8 | 6500 | 16 | 5 |
| Non-infected cells | — | — | — | — | — |

Filters:
(1)See Table 3.
(2)See Table 1.
(3)See Table 4.
(4)Calf thymus DNA, 1 μg
(5)Blank (no DNA)

Labelled nucleic acid reagents:
SV40 virus as in Table 3
Adenovirus as in Table 1
α-amylase gene as in Table 4
Hybridization:
See text of Table 1.
Washing:
See text of Table 1.

Table 5 has shown that it is possible, without division or dilution of the sample, to investigate simultaneously a series of microbes by adding a suitable reagent combination to the sample. The filters were recognized by a sign such as a mark or tag, which identified the sequence it contained.

The values in the table were corrected for reagent background, obtained by carrying out a similar hybridization without sample.

EXAMPLE 6

DNA was detected in purified *E. coli* DNA samples and in disrupted *E. coli* cells by the sandwich hybridization method in accordance with the invention.

DNA from *E. coli* K12 HB101 was isolated according to the method described by Marmur in the *Journal Molecular Biology*, Vol. 3, pp. 208-218 (1961). The DNA was denatured by treating with 7 mM NaOH at 100° C. for 5 min.

The *E. Coli* cells were treated with the following solutions: 500 μg/ml lysozyme, 70 mM EDTA at 37° C. for 30 min. and 0.25% SDS at +65° C. The free DNA was denaturated by boiling in 14 mM NaOH at +100° C. for 5 min.

The reagents were prepared from the outer membrane protein A-gene of *Escherichia coli*, called the ompA-gene. The hybrid plasmids pKTH40 and pKTH45, used as the starting materials, were prepared from the pTU100 plasmid described by Henning et al. in *Proc. Natl. Acad. Sci. USA*, Vol. 76, pp. 4360-4364 (1979).

The plasmid pKTH45 was deposited under No. EH254 at the KTL in Helsinki, Finland. This plasmid was attached to the filter. It contained 740 base pairs from the 5'-terminal end of the ompA-gene inserted into the pBR322-plasmid.

The plasmid pKTH40 contained 300 base pairs from the 3'-terminal end of the ompA-gene and the immediately following 1400 base pairs from the genome of *E. coli*. The pKTH40 plasmid was cleaved with the BamHI restriction enzyme to retrieve the DNA fragment of *E. coli*, which contained the 1700 base pairs mentioned above. This fragment was transferred to the single-stranded bacteriophage M13mp7 in accordance with the methods described by Messing et al. in *Nucleic Acids Research*, Vol. 9, pp. 309-321 (1981), Heidecker et al. in *Gene*, Vol. 10, pp. 69-73 (1980) and Gardner et al. in *Nucleic Acids Research*, Vol. 9, pp. 2871-2888 (1981).

The recombination-phage mKTH1207 was deposited under No. EH256 at the KTL. This recombination-phage was labelled with an $^{125}$I-isotope as described under the heading "Other labelling methods" and was used as a probe in the sandwich hybridization method.

As shown in Table 6, the *E. coli* was identifiable by sandwich hybridization on the basis of the outer membrane protein A-gene.

TABLE 6

| Samples | Filters (cpm) | | |
|---|---|---|---|
| | ompA (1) | Calf thymus (2) | Blank (3) |
| *E. coli* K12 HB101 DNA (a) $2 \times 10^7$ | 282 | — | — |
| *E. coli* K12 HB101 DNA (a) $2 \times 10^8$ | 2206 | — | — |
| *E. coli* K12 HB101 cells (b) $2 \times 10^7$ | 1113 | — | — |
| *E. coli* K12 HB101 cells (b) $2 \times 10^8$ | 2327 | 12 | 5 |

(a)number of DNA-molecules
(b)number of cells
Filters:
(1)pKTH45 plasmid 1.088 μg ($2 \times 10^{11}$ molecules)
(2)Calf thymus DNA 1.088 μg
(3)Blank (no DNA)

Labelled nucleic acid reagent:
mKTH1207, specific activity $8 \times 10^7$ cpm/μg DNA (200,000 cpm/reaction)
Hybridization:
4×SSC, 1×Denhardt solution without BSA (bovine serum albumin), containing 200 μg/ml Herring sperm DNA and 0.25% SDS, at +65° C. for 17.5 hours
Washing:
See text of Table 1.

The values presented in the table have been corrected for reagent background, obtained from a similar hybridization without sample.

We claim:

1. A method for identifying nucleic acids by a one-step sandwich hybridization test, said method comprising the steps of:
   (a) rendering the nucleic acids in the sample to be identified single-stranded;
   (b) allowing said single-stranded nucleic acids of the sample to hybridize simultaneously in a single step with a combination of at least one pair of nucleic acid reagents, said reagents having been purified, the first nucleic acid reagent of said pair comprising a single-stranded fragment of nucleic acid, having a nucleotide sequence of at least 10 bases, and being affixed to a solid carrier, the second nucleic acid reagent of said pair comprising a single-stranded fragment of nucleic acid, having a nucleotide sequence of at least 10 bases, and being labeled with a radioisotope, said first and second nucleic acid reagents being capable of forming hybrid molecules by complementary base pairing with given sequences of the sample nucleic acid to be identified, provided that the second nucleic acid reagent cannot hybridize with the first nucleic acid reagent;
   (c) washing said solid carrier to substantially remove said label which is not incorporated in said hybrid molecule; and
   (d) measuring said label on the washed solid carrier, whereby determining whether the sample contains the nucleic acid to be identified.

2. The method of claim 1, wherein the first nucleic acid reagent is a DNA or RNA fragment.

3. The method of claim 1, wherein the second nucleic acid reagent is a DNA or RNA fragment.

4. The method of claim 1, wherein the solid carrier is a nitrocellulose sheet.

5. A kit for the detection of nucleic acids with a one-step sandwich hybridization test, the kit comprising in packaged combination a container of at least one pair of nucleic acid reagents, said reagents having been purified:
   (a) a first nucleic acid reagent of said pair comprising a single-stranded fragment of nucleic acid, having a nucleotide sequence of at least 10 bases, and being affixed to a solid carrier, said first nucleic acid reagent being capable of forming a double-stranded hybrid molecule by complementary base pairing with a given sequence of the nucleic acid to be identified and
   (b) a second nucleic acid reagent of said pair comprising a single-stranded fragment of nucleic acid having a nucleotide sequence of at least 10 bases, and being labeled with a radioisotope, said second nucleic acid reagent being capable of forming a double-stranded hybrid molecule by complementary base pairing with a given sequence of the nucleic acid to be identified, provided that the second nucleic acid reagent cannot hybridize with the first nucleic acid reagent.

6. The diagnostic kit of claim 5, wherein the first nucleic acid reagent is a DNA or RNA fragment.

7. The diagnostic kit of claim 5, wherein the second nucleic acid reagent is a DNA or RNA fragment.

8. The diagnostic kit of claim 5, wherein the solid carrier is a nitrocellulose sheet.

* * * * *